United States Patent
Soffiatti et al.

(10) Patent No.: US 10,251,753 B2
(45) Date of Patent: Apr. 9, 2019

(54) ELBOW SPACER

(71) Applicant: TECRES S.p.A., Sommacampagna (Verona) (IT)

(72) Inventors: Renzo Soffiatti, Nogara (IT); Giovanni Faccioli, Monzambano (IT)

(73) Assignee: TECRES S.P.A., Sommacampagna (VR) (IT)

( * ) Notice: Subject to any disclaimer, the term of this patent is extended or adjusted under 35 U.S.C. 154(b) by 8 days.

(21) Appl. No.: 15/519,991

(22) PCT Filed: Sep. 29, 2015

(86) PCT No.: PCT/IB2015/057456
§ 371 (c)(1),
(2) Date: Apr. 18, 2017

(87) PCT Pub. No.: WO2016/063155
PCT Pub. Date: Apr. 28, 2016

(65) Prior Publication Data
US 2017/0312086 A1     Nov. 2, 2017

(30) Foreign Application Priority Data
Oct. 21, 2014 (IT) ............... VR2014A0258

(51) Int. Cl.
    *A61F 2/38*     (2006.01)
    *A61F 2/30*     (2006.01)

(52) U.S. Cl.
    CPC .... *A61F 2/3804* (2013.01); *A61F 2002/3092* (2013.01); *A61F 2002/30624* (2013.01); *A61F 2002/30672* (2013.01); *A61F 2002/30677* (2013.01); *A61F 2002/3813* (2013.01); *A61F 2002/3822* (2013.01); *A61F 2002/3831* (2013.01); *A61F 2310/00353* (2013.01)

(58) Field of Classification Search
CPC ............ A61F 2/3804; A61F 2002/3813; A61F 2002/3822; A61F 2002/3831; A61F 2002/30624
See application file for complete search history.

(56) References Cited

U.S. PATENT DOCUMENTS

| | | |
|---|---|---|
| 3,708,805 A | 1/1973 | Scales et al. |
| 2006/0052725 A1 | 3/2006 | Santilli |
| 2007/0179609 A1 | 8/2007 | Goble et al. |
| 2013/0345818 A1* | 12/2013 | Wagner ................. A61F 2/3804 623/20.12 |

* cited by examiner

*Primary Examiner* — Brian Dukert
(74) *Attorney, Agent, or Firm* — Tutunjian & Bitetto, P.C.

(57) ABSTRACT

The present invention regards an elbow spacer device, including: at least one ulnar section, including a stem portion extending along a substantially longitudinal axis (x-x) between a proximal end and a distal end; at least one humeral section, including a stem portion extending along a substantially longitudinal axis (y-y) between a proximal end and a distal end, the distal end of the humeral section delimiting an engagement seat with the proximal end of the ulnar section; articulation means between the distal end of the humeral section and the proximal end of the ulnar section, positionable along an axis (z-z) that is orthogonal to the substantially longitudinal axis (y-y) of the humeral section. The proximal end of the ulnar section is engageable in the housing seat.

31 Claims, 9 Drawing Sheets

FIG. 10

ELBOW SPACER

TECHNICAL FIELD OF THE INVENTION

The present invention regards a spacer device for the elbow joint, particularly employable in the treatment of infections according to the so-called "two-stage" treatment.

STATE OF THE PRIOR ART

The elbow joint, although it is often considered to be a single articulation, comprises three separate articulations, associated with a single capsule. These are the humeroradial articulation, the humeroulnar articulation, which allows the bending and extending movements of the forearm on the arm, and the proximal radioulnar articulation, which allows the prono-supination of the hand.

The present invention regards a spacer device that affects the humeroulnar joint.

STATE OF THE PRIOR ART

In the treatment of elbow lesions, which require the implant of a prosthesis, the tissues surrounding the prostheses may become infected.

The explant of the prosthesis is therefore necessary for treating the infection, and once the infected tissues have healed, it is necessary to implant a new permanent prosthesis.

Such method for treating the infection is usually defined two-stage treatment, since it provides for a first step for removing the prosthesis and a second step for implanting a new prosthesis, once the infection has been eliminated.

The treatment of the infection requires the use of a spacer device which, in addition to maintaining the articular portions suitably spaced from each other during treatment, comes into contact or is interfaced with the space left free by the removed prosthesis and gradually releases antibiotic or another active ingredient suitable for treating the specific infection, with consequent treatment of the infection itself.

One such spacer device also allows a patient to maintain at least a partial mobility of the treated limb.

The spacer devices currently on the market are negatively affected by the drawback that, even if they allow suitably maintaining the articular portions spaced during the treatment stage, they do not allow any mobility of the limb. There is therefore the need to arrange a spacer device for the elbow joint that has an alternative configuration with respect to the conventional spacers, which allows the mobility of the limb after its implant and, simultaneously, is easy to assemble and implant in the limb of a patient.

SUMMARY OF THE INVENTION

The technical task of the present invention is to improve the state of the art in the field of spacer devices for the elbow joint.

In the scope of such technical task, one object of the present invention is to provide a spacer device for the treatment of infections at the elbow joint which has an alternative configuration with respect to that of the conventional spacer devices.

Another object of the present invention is to provide a spacer device for the treatment of infections at the elbow joint which allows the articular mobility once this has been implanted in situ.

Still another object of the present invention is to provide a spacer device for the treatment of infections at the elbow joint which is composed of a reduced number of components.

A further object of the present invention is to provide a spacer device for the treatment of infections at the elbow joint which can be obtained at competitive costs.

Not least object of the present invention is to provide a spacer device for the treatment of infections at the elbow joint which is easy to assemble.

In accordance with one aspect of the present invention, a spacer device is provided for the treatment of infections at the elbow joint according to the present application.

In accordance with another aspect of the present invention, a method is provided for assembling a spacer device for the treatment of infections at the elbow joint according to the present application.

The present specification refers to preferred and advantageous embodiments of the invention.

BRIEF DESCRIPTION OF THE DRAWINGS

Further characteristics and advantages of the present invention will be clearer from the detailed description of several preferred embodiments of a spacer device for the treatment of infections of elbow prostheses, illustrated by way of a non-limiting example, in the enclosed drawing tables in which.

In the enclosed drawings, equivalent parts or components are marked by the same reference numbers.

DETAILED DESCRIPTION OF THE INVENTION

With reference to the enclosed figures, reference number 1 overall indicates a spacer device according to the present invention for the treatment of infections at the elbow joint, in particular a temporary spacer device to be used during the two-stage treatment of infections, during the time from the explant of a first prosthesis and the implant of a second prosthesis, in order to treat the infection underway at the implant site.

The spacer device 1 is capable of maintaining the articular space and ensuring the articulation of the elbow up to the implant of the new prosthesis, at the same time treating the infection due to the presence, in the spacer device itself, of suitable drugs or medications, such as one or more antibiotics and by means of the contact of the device with the entire infected area to be treated.

The spacer device 1 according to the present invention is made of biologically compatible material, additionated and/or additionable with one or more pharmaceutical products, active and/or therapeutic ingredients intended to be released into the tissues of the patient surrounding the device.

The biologically compatible material of the spacer device 1 according to the present invention is porous, in particular comprises pores that may or may not be interconnected.

The material for the spacer device 1 according to the present invention can be selected from among the following materials: metals, metallic alloys, organic metals, ceramic, glass, plastic materials.

More particularly, the plastic materials may comprise at least one from among: thermoplastic polymers, such as acrylic resins, including all copolymers and acrylic mixtures, polyethylene, polypropylene, etc.

In one version of the invention, the biologically compatible material with which the spacer device 1 is obtained comprises a bone cement or polymethyl methacrylate.

The material of the spacer device according to the present invention can comprise one or more pharmaceutical products, active and/or therapeutic ingredients.

The pharmaceutical products, active and/or therapeutic ingredients can comprise antibiotics, antiseptics, bacteriostatic agents, bactericides, antimycotics, chemotherapeutic agents, e.g. gentamicin, vancomycin, etcetera, or other active ingredients.

The material of the spacer device, being porous, can be added with the drug during production stage, or afterward by the doctor at the time of implant in the patient, e.g. via impregnation. If the spacer device is already provided comprising a pharmaceutical product, an active and/or therapeutic ingredient, it can be subsequently added with further one or more pharmaceutical products, active and/or therapeutic ingredients with the purpose of enlarging the action spectrum or introducing a medication that is highly specific for the identified pathogenic agent. Such further substances may be different from the pharmaceutical products, active and/or therapeutic ingredients already comprised in the spacer device, in order to enlarge the application range thereof. As an example of antibiotic additions, it is possible to provide for the following cases: to the gentamicin originally present, the doctor can add vancomycin to oppose the Gram-positive bacteria, or clindamycin for opposing anaerobic bacteria. In order to do this, it is possible, for example, to immerse the spacer device in an aqueous antibiotic solution. The solution will be absorbed together with the antibiotic in the mass of the spacer in a few minutes. The quantity of absorbed solution can be modified as desired by virtue of the structure of the material. Optimal values are comprised between 1 and 60% by weight of absorbed solution. In other words, if the spacer weighs 100 grams, in accordance with its structure, it can absorb from 1 to 60 grams of medicated aqueous solution.

The spacer device 1 according to a first embodiment of the present invention comprises at least one ulnar section 2, at least one humeral section 3 delimiting an engagement seat 4 and articulation means 5, at such engagement seat 4, intended to achieve the engagement and the articulation between the ulnar section 2 and the humeral section 3.

More particularly, the ulnar section 2 has a stem portion 6, which is extended along a substantially longitudinal axis x-x between a proximal end 7 and a distal end 8.

The humeral section 3 has a stem portion 9, which extends along a substantially longitudinal axis y-y between a proximal end 10 and a distal end 11. The distal end 11 of the humeral section 3 delimits, as stated above, an engagement seat 4 with the proximal end 7 of the ulnar section 2.

The articulation means 5 between the distal end 11 of the humeral section 3 and the proximal end 7 of the ulnar section 2, as will be better stated hereinbelow, are, during use, arranged in the engagement seat 4, along an axis z-z that is orthogonal to said substantially longitudinal axis y-y of the humeral section 3.

The humeral section 3 of the spacer device according to the present invention has the stem portion 9 tapered towards its proximal end 10 and has an in use front face 12, an in use rear face 13 and two right and left in use side faces, right and left, respectively indicated in the figures with the numbers 14 and 15. The distal end 11 of the humeral section 3 is configured to be substantially fork-shaped and comprises two sides 16, 17, a right one and a left one during use, each extended from the stem portion 9 at a respective in use side face, 14 or 15, substantially along the axis y-y.

The distal end 11 of the humeral section 3 also comprises a front wall 18 for connection between the sides 16 and 17 and connected to the stem 9 at the in use front face 12. Such front wall 18 substantially extends in a cantilevered manner from the in use front face 12. The distal end 11 also comprises a rear wall 18' for connection between the sides 16 and 17 and connected to the stem 9 at the in use rear face 13 roughly coplanar therewith.

The sides 16 and 17, the in use front wall 18 and the in use rear wall 18' delimit the engagement seat 4.

Figure 1:
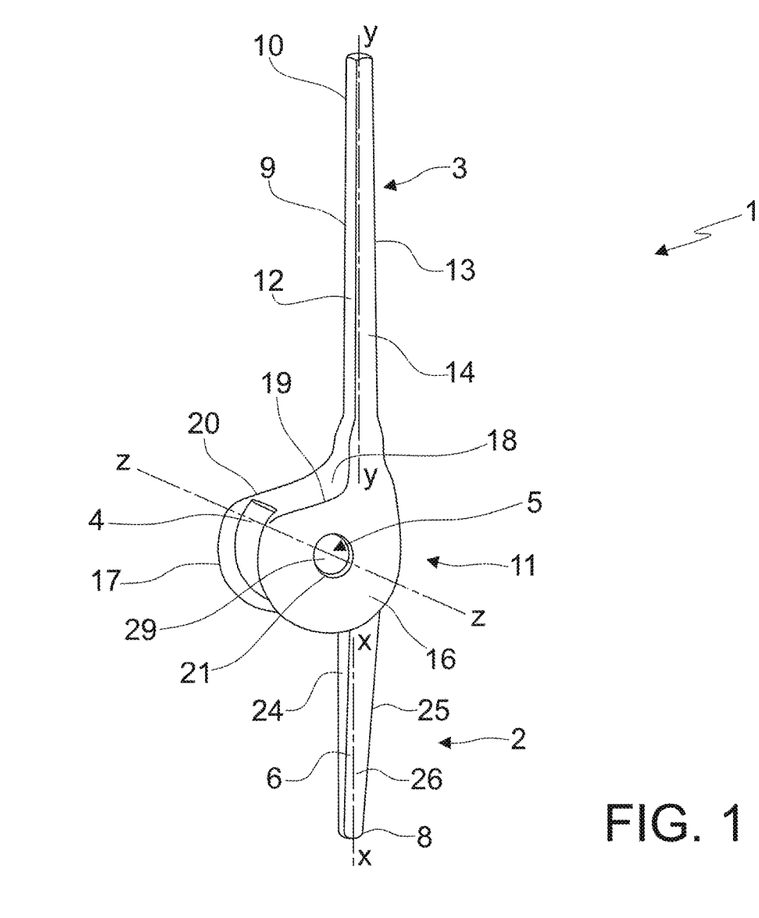
FIG. 1 is a side elevation perspective view of a spacer device according to a first embodiment of the present invention.
Figure 2:
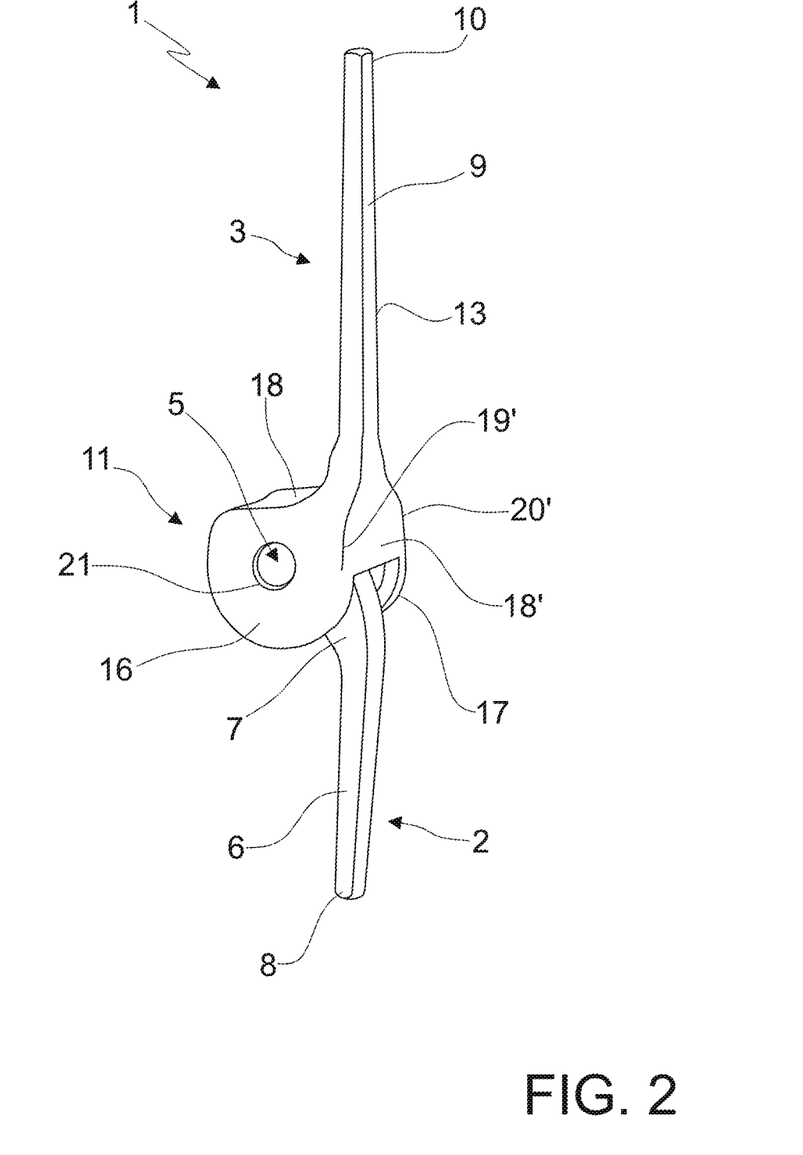
FIG. 2 shows a rear perspective view of the spacer device of FIG. 1.

As will be observed, each side 16 or 17 of the distal end 11 of the humeral section 3, viewed laterally, has a substantially rounded configuration (FIGS. 1 and 2) with a first substantially rectilinear section 19 or 20 at the connection with the front wall 18 and a second section also substantially rectilinear 19' or 20' at the connection with the in use rear wall 18'. In addition, sides 16 and 17, viewed frontally, have an increasing thickness (FIGS. 3 to 9), moving away from the stem portion 9. Advantageously, the engagement seat 4 also has its own cross section, with respect to the longitudinal axis y-y, increasing moving away from the stem portion 9. With one such configuration, in the engagement seat 4, the sides 16 and 17 are at a minimum distance 23 near the front wall 18 and at a maximum distance at the most extreme points (with respect to the stem 9) of the sides 16 and 17. With one such configuration, it will be easily understood that an optimal distribution is obtained of the forces exerted on the ulnar section 2 and on the humeral section 3 during the use of the spacer device itself, i.e. during the bending-extending movements of the limb in which such spacer device is implanted.

In each side 16, 17 of the distal end 11, at least one through opening 21, 22 is obtained, in the example illustrated in the figures only one opening per side. The at least one opening on each side 16 or 17 is aligned with at least one other opening in the other side 17 or 16 of the distal end 11, along a common axis, in the specific case illustrated in the drawings as axis z-z. At such axis, as will be better explained hereinbelow, the articulation means 5 are arranged during use. Returning to the ulnar section 2 of the spacer device 1 according to the first embodiment of the present invention, this has its own stem portion 6 tapered towards its distal end 8 and has an in use front face 24, an in use rear face 25 and two in use side faces, right and left, respectively indicated in the figures with the reference numbers 26 and 27.

Each face 26 and 27, at the proximal end 7 of the ulnar section 2, has a substantially flat and enlarged configuration, with respect to the corresponding distal end 8 of the stem portion. More particularly, at the proximal end 7, each face 26 and 27 has a substantially round, roughly circular configuration.

As will be observed, see in particular FIGS. 5 to 9, the ulnar section 2 is sized such that the transverse size of its proximal end 7 is smaller than the minimum transverse size (minimum distance 23) of the engagement seat 4 of the humeral 5 section 3, so that it is insertable therein with a certain clearance and, more particularly, it can be moved with a side face 26 or 27 thereof in contact with either side 16 or 17 of the seat itself.

In the ulnar section 2, at the proximal end 7, at least one through opening 28 is obtained, which, during use, is intended to receive the articulation means 5 of 10 the spacer device 1 according to the present invention, as will be better stated hereinbelow.

Figure 7:
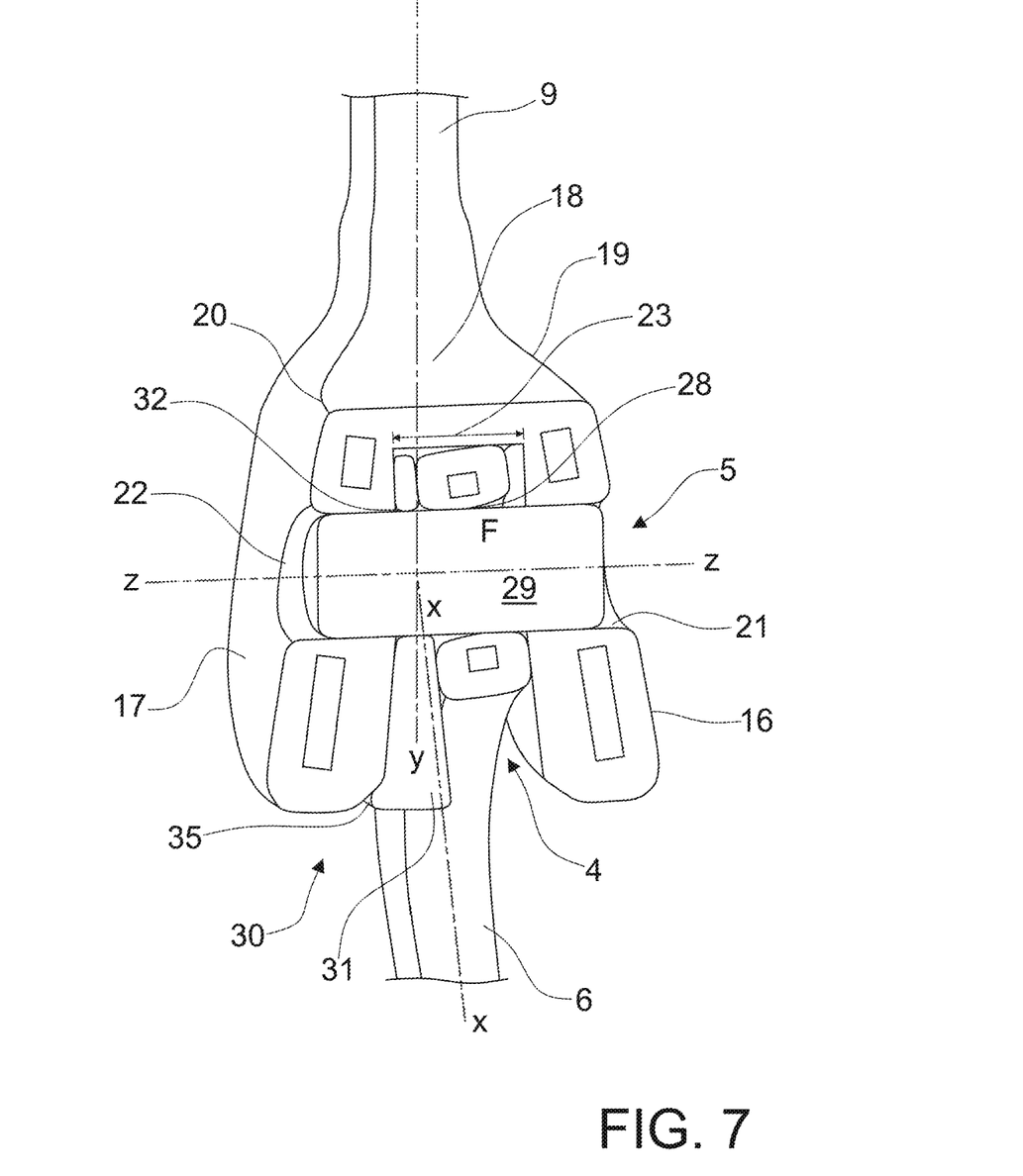
FIG. 7 shows an enlarged scale and cross section view taken along a front plane of the spacer device according to the first embodiment of the present invention, with the ulnar section arranged according to the second working position.

Such through opening 28 delimits a gap with substantially hourglass configuration, i.e. with minimum cross section, indicated in FIG. 7 with the letter F, at a longitudinal symmetry plane (not illustrated in the drawings) of 15 the ulnar section 2 passing through the abovementioned axis x-x. Such gap has increasing cross section moving away from such longitudinal symmetry plane. The articulation means 5 of the spacer device 1 according to the present invention advantageously comprise at least one pin 29, with cross section corresponding to the minimum gap delimited by the through opening 28 and by 20 the through openings 21 and 22 on the sides 16 and 17 of the distal portion 11 of the humeral section 3.

The pin 29 is therefore engageable with the ulnar section 2, without clearance, only at the minimum cross section of the opening 28. The side wall of the ulnar section 2 delimiting such through opening 28 may or may not touch the pin 29, 25 in accordance with how the ulnar section 2 is, during use, arranged in the engagement seat 4.

Indeed, with one such configuration, the proximal end 7 of the ulnar section 2, inserted in the engagement seat 4, can slightly move along the axis z-z and complete a slight angular travel around a pivot at the minimum cross section of 30 the opening 28, indicated with F.

Therefore, as will be observed, the proximal end 7 of the ulnar section 2 is engageable in the housing seat 4 of the humeral section 2 with its own longitudinal axis x-x not orthogonal to the axis z-z along which the pin 29 is arranged, between at least two opposed working positions, according to 5 whether the spacer device is intended to be implanted in the right or left upper limb of a patient.

In the first working position (FIG. 5), the proximal end of the ulnar section 2 is situated in the engagement seat 4 adjacent to the side 17 and, therefore, has its own longitudinal axis x-x shifted by −θ° with respect to the axis y-y of the humeral section. In this first working position, the spacer device according to the present invention is suitable for being inserted in the upper right limb of a patient.

In the second working position, however, the proximal end of the ulnar section 2 is situated in the engagement seat 4 adjacent to the side 16 (FIGS. 6 and 7) 15 and, therefore, has its own longitudinal axis x-x shifted by +θ° with respect to the axis y-y of the humeral section. In this second working position, the spacer device according to the present invention is usable in order to be inserted in the upper left limb of a patient.

Figure 10:
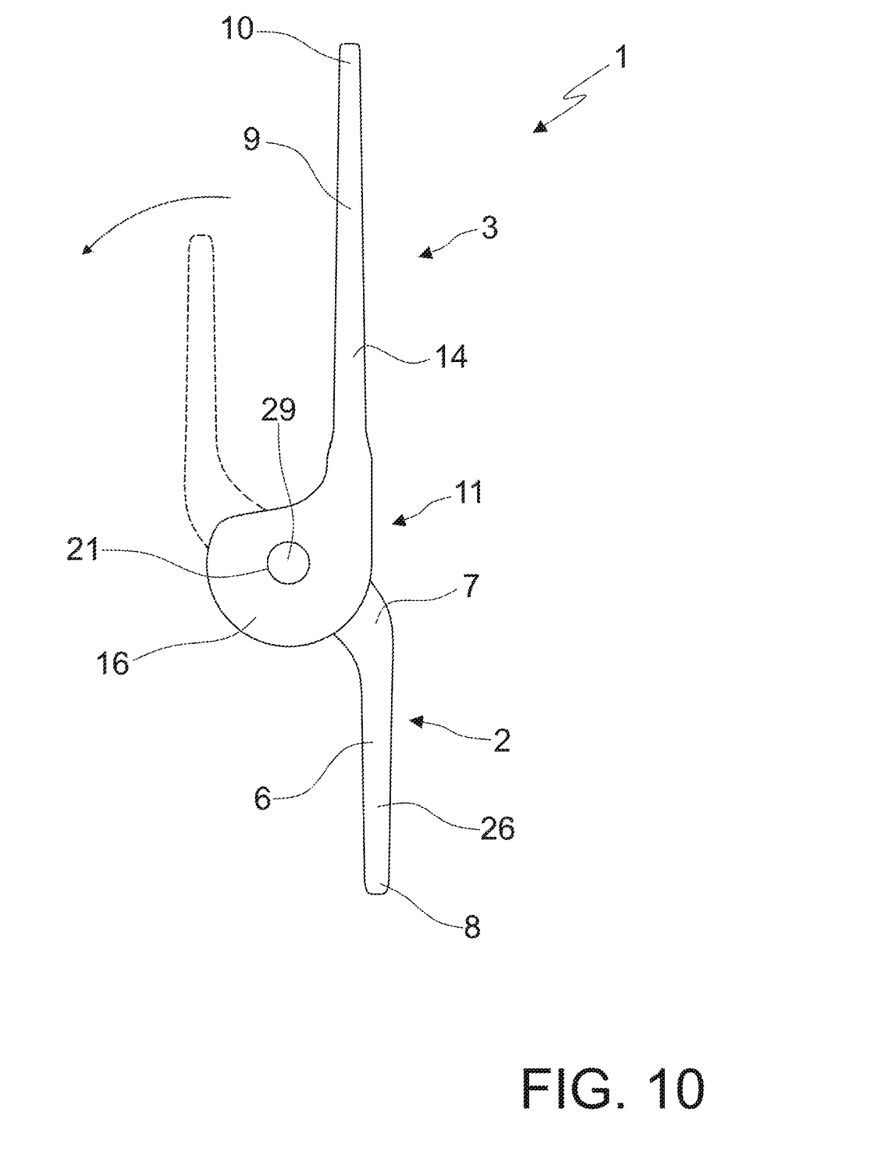
FIG. 10 shows the spacer device according to the first or second embodiment in two work positions, one for bending and one for extending the device itself.

Independent of the working position assumed by the ulnar section 2, the spacer 20 device according to the present invention is sized such that the proximal portion 7 of the ulnar section 2, once inserted in the engagement seat 4 of the humeral section 3, and once the pin 29 is subsequently inserted in the through openings 21, 22 and 28 of the sides 16 and 17 and of the ulnar section 2, is rotatable around the pin 29 (as indicated in FIG. 10) between a bend position, 25 in which it is situated substantially facing the humeral section 3 and touches the front wall 18, and an extension position, in which it is situated substantially moved away from the humeral section 3, aligned therewith. As will be observed, the spacer device according to the present invention allows the ulnar section 2, in the position of maximum extension, to touch the in use rear wall implanted in patients with reduced humeral brachial flexion, the extension of the forearm on the arm and hence of the spacer device is self-limited and in fact the ulnar section 2 never touches the in use rear wall 18' of the humeral section 3.

The spacer device according to the first embodiment of the present invention comprises means 30 for orienting the ulnar section 2 with respect to the humeral section 3, housable in the engagement seat 4.

Such orientation means 30 are provided for being interposed, in the engagement seat 4, between the proximal portion 7 of the ulnar section 2 and either side 16 or 17 of the seat 4.

Preferably, the orientation means 30 comprise a bush means, e.g. made of polyethylene, fittable on the articulation means 5, or any other suitable means capable of maintaining the proximal portion 7 of the ulnar section 2 adjacent to either side 16 or 17. Included among these are wedge or tilted-wall means.

Figure 3:
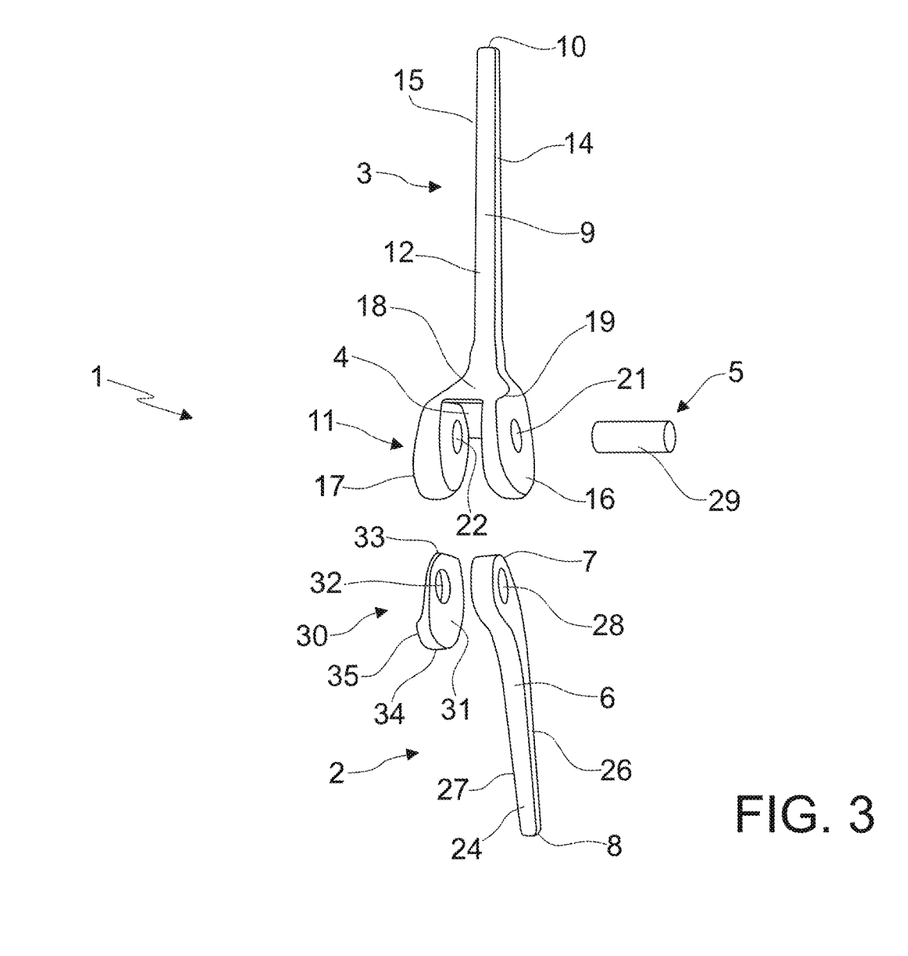
FIG. 3 illustrates an exploded view of the device of FIG. 1.
Figure 4:
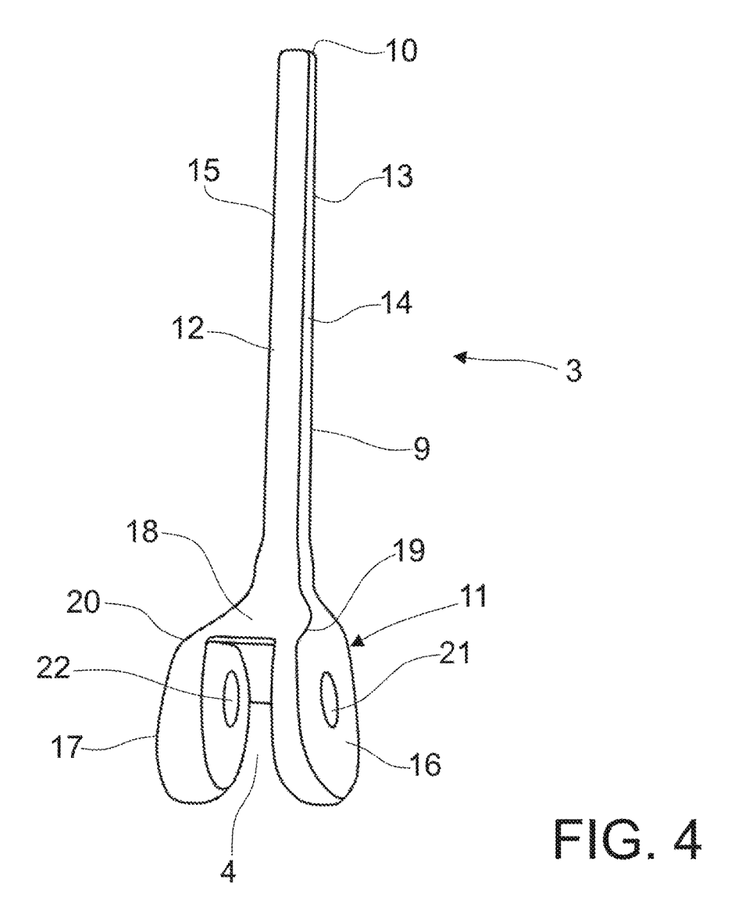
FIG. 4 is a perspective view, in front elevation, of a humeral section of the device of FIG. 1.

In the described embodiment and with particular reference to FIGS. 3 and 7, it will be observed that the orientation means 30 are advantageously configured as an annular plate 31 and delimit a through opening 32 of size roughly corresponding to that of the gap delimited by the openings 21 and 22 respectively on the sides 16 and 17 of the humeral section 3. Such annular plate 31 can be fit on the pin 29 and has a minimum thickness at its proximal section 33 intended, during use, to be housed in the engagement seat 4 facing the in use front wall 18 of the humeral section 3. At such section, the annular plate 31 has a perimeter configuration with rectilinear sections, roughly corresponding to the internal configuration of the seat 4 between the in use front 18 and in use rear 18' walls.

The thickness of the annular plate instead has its maximum at an opposite or distal section 34, i.e. during use facing away from the stem 9 of the humeral section.

The annular plate 31 has its own face directed towards either side 16 or 17 of the humeral section 3, configured in a manner corresponding to the face of such side directed towards the engagement seat 4. The annular plate 31 has a flange 35 at its opposite or distal section 34. Such flange 35 and the configuration of the annular plate 31 at its proximal section 33, as well as the configuration of its side faces contribute to ensuring that it remains stopped in position, once it is housed in the seat 4 and fit on the pin 29.

With one such configuration of the spacer device according to the first embodiment of the present invention, it is clear that its assembly is quite simple and comprising the operating steps of arranging at least one humeral section 3, at least one ulnar section 2, and at least the aforesaid articulation means 5. Such sections will have size suitable for the articular dimensions of the patient.

Then, provision is made for inserting the proximal end 7 of the ulnar section 2 in the engagement seat 4 of the humeral section 3, with the through openings of the respective sections 21, 22 and 28 aligned with each other along a common axis z-z.

Subsequently, if the spacer device 1 is intended to be implanted in the upper right limb of a patient, the assembly of the spacer device according to the present invention provides for orienting the ulnar section 2, in the engagement seat 4, in a manner such that it has its own longitudinal axis x-x shifted by an angle −θ°, with respect to the axis y-y of the humeral section 3. Otherwise, if the spacer device 1 is intended to be implanted in the upper left limb of a patient, the assembly method provides for orienting the ulnar section 2 in a manner such that it has its own longitudinal axis x-x shifted by an angle +θ°, with respect to the axis y-y.

Once the ulnar section 2 of the device is brought into the desired first or second work position, the orientation means 30 are inserted in the seat, so as to angularly lock the ulnar section 2 by ±9° with respect to the axis y-y of the humeral section.

If the orientation means 30 comprise the annular plate 31 as described above, it will be inserted in the engagement seat 4 in a manner such that its through opening 32 is aligned with the through openings 21, 22 and 28 along the common axis z-z.

Subsequently, provision is made for inserting the articulation means 5 (the pin 29) into the abovementioned through openings.

It should be observed that the latter step of inserting the articulation means 5 in the openings can also occur before the step of orienting the ulnar section 2 towards either one of the sides 16 or 17 of the distal portion 11 of the humeral section, if the orientation means 30 do not require being fit on the pin 29.

Figure 8:
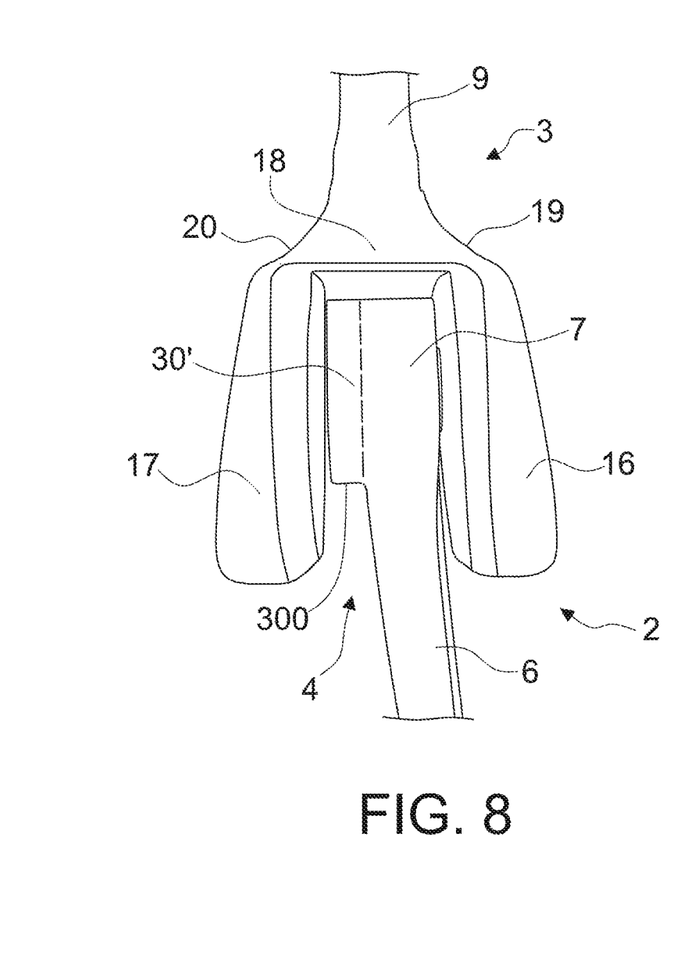
FIGS. 8 and 9 respectively illustrate a front view of a spacer device according to a second embodiment of the present invention and a view thereof in longitudinal section taken along a front plane of the device.
Figure 9:
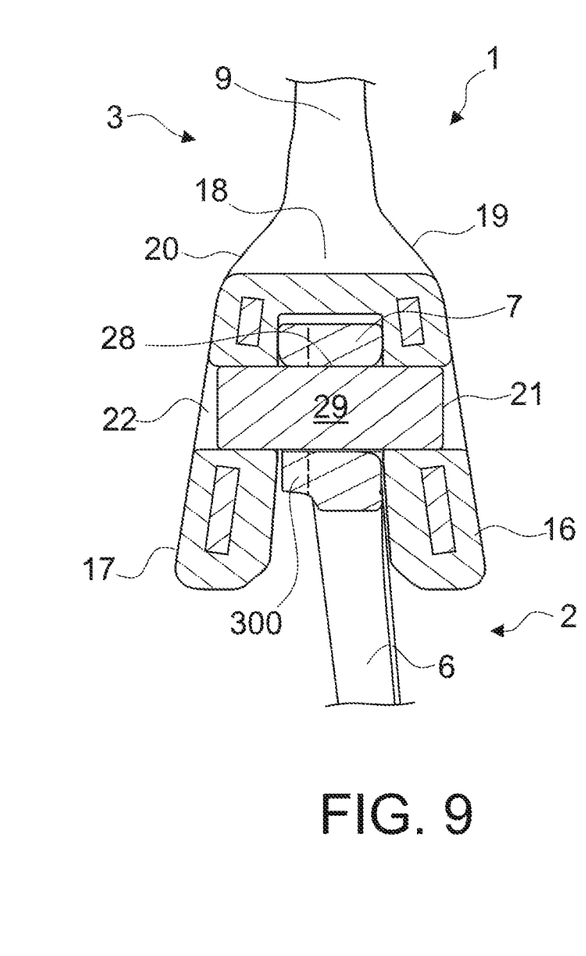

The spacer device according to the present invention comprises a second embodiment, illustrated in FIGS. 8 and 9, which differs from the first embodiment since the ulnar section 2 and the orientation means 30 are integrally obtained.

In this case, as is clear, the orientation means 300 are also configured as an annular plate 301 and delimit a through opening 302 of size roughly corresponding to that of the openings 21 and 22 on the sides 16 and 17 of the humeral section 3 and of the through opening 28 of the ulnar section 2. Such annular plate 301, according to whether the spacer device must be implanted on the right or left limb of a patient, is provided on the face 26 or 27 of the ulnar section itself, so that—depending on the case—the ulnar section is during use adjacent to the side 16 or 17 of the humeral section 3.

In this case, since the orientation means are moved around the pin 29 together with the ulnar section 2, they have a transverse configuration such to not prevent the rotation of the ulnar section within the engagement seat 4. In the specific case illustrated in the figure, the orientation means 300 have a circular crown shaped cross section.

In this second embodiment, as will be observed, the gap delimited by the through opening 28-302 of the ulnar section has constant cross section.

Thus, it is seen that the above-described spacer device clearly solves the abovementioned technical problems, since it has a configuration entirely alternative with respect to the spacer devices of conventional type, it comprises a reduced number of components and is also very simple to assemble.

Moreover, one such spacer device, comprising a stem portion both on the ulnar section 2 and on the humeral section 3, in turn allows being inserted in respective bone portions of a patient to be treated, thus ensuring the articular mobility and the effective delivery of the antibiotic treatment over a vast area. The above-described spacer device 1 is susceptible of numerous modifications and variants within the protective scope of the following claims.

Figure 5:
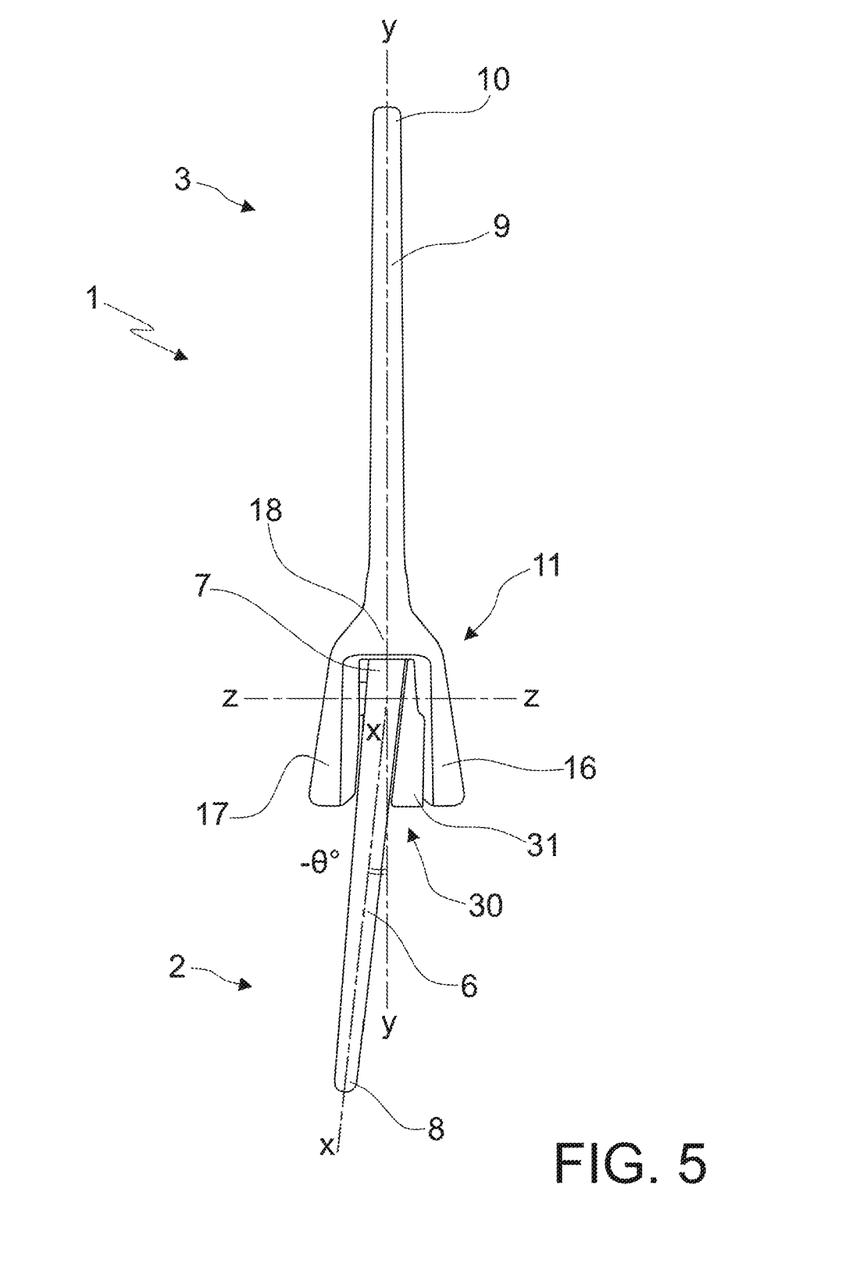
FIG. 5 shows a front view of the device of FIG. 1, with an ulnar section arranged according to a first working position.
Figure 6:
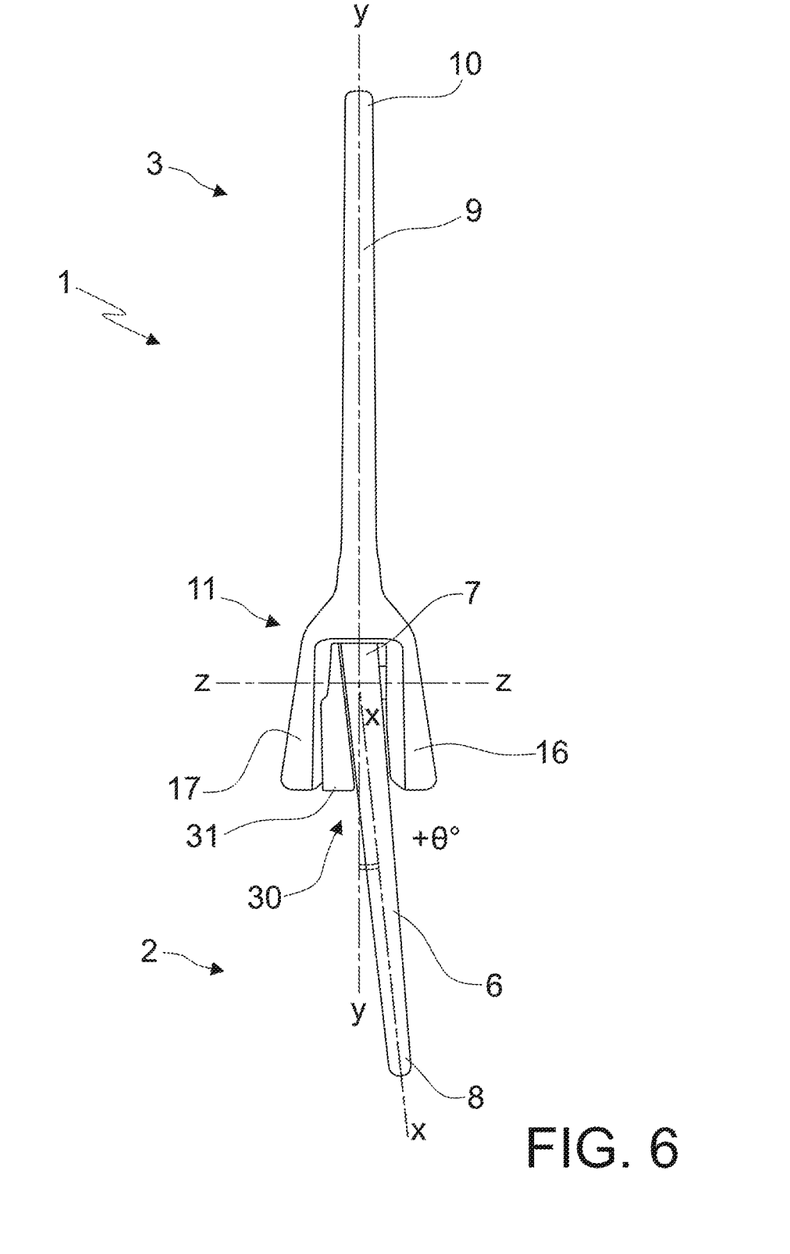
FIG. 6 illustrates a front view of the device of FIG. 1, with an ulnar section arranged according to a second working position.

As is seen for example in FIG. 5, both the ulnar section 2 and the humeral section 3 comprise a stiffening core, preferably made of metallic material, which contributes to making the spacer device more stress resistant. In addition, if possible, for example in the ulnar section 2 in the region comprised between the stem 6 and the proximal end 7, one or more through openings can be made in the stiffening core, which perform the function of reducing the weight thereof while maintaining the core's mechanical characteristics of stress resistance unaltered.

Finally, in accordance with case requirements, it is possible to provide that the stem portion 6 of the ulnar section 2, even if mainly extended along the rectilinear axis x-x, has a medial-distal section not aligned with such axis in order to be better adapted to the anatomy of the patient being treated.

The invention claimed is:

1. A spacer device for the treatment of infections at the elbow joint, comprising:
    at least one ulnar section, comprising a stem portion extending along a substantially longitudinal axis (x-x) between a proximal end and a distal end;
    at least one humeral section, comprising a stem portion extending along a substantially longitudinal axis (y-y) between a proximal end and a distal end;
    at least one engagement seat between said distal end of said at least one humeral section and said proximal end of said at least one ulnar section, said at least one engagement seat being delimited by said at least one humeral section; and
    articulation means between said distal end of said at least one humeral section and said proximal end of said at least one ulnar section, positionable along an axis (z-z) orthogonal to said substantially longitudinal axis (y-y) of said at least one humeral section;
    wherein said proximal end of said at least one ulnar section is engageable in said engagement seat, said proximal end having its own longitudinal axis (x-x) nonorthogonal to said axis (z-z) of said articulation means, according to at least two opposed working positions, according to whether said spacer device is designed to be implanted in the right or in the left upper limb of a patient.

2. The spacer device according to claim 1, wherein the transverse size of said proximal end of said ulnar portion is smaller than the transverse size cross-section delimited by said engagement seat of said at least one humeral section.

3. The spacer device according to claim 1, wherein said engagement seat has an increasing cross section size, moving away from said stem portion along said longitudinal axis (y-y).

4. The spacer device according to claim 1, wherein said at least one humeral section is provided with said stem portion tapered toward said proximal end and includes a front, in use, face, a rear in use face, and two left and right in use side faces.

5. The spacer device according to claim 4, wherein said distal end of said at least one humeral section is configured to be substantially fork-shaped and comprises:

two sides, in use a right one and a left one, each extending from said stem portion in correspondence with a respective in use side face substantially along said axis (y-y);

an in use front wall for connection between said sides connected to said stem at said front, in use, face and substantially extending from it in a cantilevered manner; and an in use rear wall, for connection between said sides connected to said stem at said in use rear face, and substantially extending therefrom along said axis (y-y);

said sides and said in use front wall and said in use rear wall delimiting said engagement seat.

6. The spacer device according to claim 5, wherein said sides have a substantially rounded shape with a substantially straight section at said connection with said in use front wall and in use rear wall, respectively.

7. The spacer device according to claim 5, wherein at least one through opening is formed in each side.

8. The spacer device according to claim 7, wherein said at least one through opening of one of said sides is aligned with said at least one through opening of the other of said sides along an axis, said axis being coincident with said axis (z-z) for said articulation means.

9. The spacer device according to claim 5, wherein said sides have a thickness which increases in a direction away from said stem portion.

10. The spacer device according to claim 5, wherein said sides are at a minimum distance near said front in use wall.

11. The spacer device according to claim 1, wherein said at least one ulnar section is provided with said stem portion tapered toward said distal end and comprises one front in use face, one rear in use face, and two right and left side in use faces.

12. The spacer device according to claim 11, wherein said proximal end of said at least one ulnar portion, viewed laterally, presents a substantially flat and enlarged configuration with respect to the corresponding portion near said distal end.

13. The spacer device according to claim 7, wherein said articulation means comprise at least one pin, the cross-section thereof corresponding to the gap delimited by said aligned through openings in said sides of said distal portion of said humeral section.

14. The spacer device according to claim 11, wherein, between said side in use faces of said proximal end of said at least one ulnar section, at least one through opening is formed defining a gap substantially hourglass-shaped, with a minimum cross section (F) at a longitudinal symmetry plane of said at least one ulnar section including said axis (x-x), and increasing moving away therefrom.

15. The spacer device according to claim 14, wherein said minimum cross section (F) of said gap delimited by said through opening substantially corresponds to a cross section of a pin, so that said pin is insertable in said through opening, without clearance only at said minimum cross section (F).

16. The spacer device according to claim 15, wherein said proximal end of said at least one ulnar section, inserted in said engagement seat, can slightly move along said axis (z-z) and complete a slight angular travel at said minimum cross section (F) of said through opening.

17. The spacer device according to claim 11, wherein between said side in use faces, of said proximal end of said at least one ulnar section, at least one through opening is obtained delimiting a gap having a constant cross section.

18. The spacer device according to claim 5, comprising orienting means of said at least one ulnar section with respect to said at least one humeral section, said orienting means being positionable between said at least one ulnar section and said at least one humeral section in said at least one engagement seat.

19. The spacer device according to claim 18, wherein said orienting means are placed, in said seat of engagement, between said proximal portion of said at least one ulnar section and either one of said sides delimiting said seat.

20. The spacer device according to claim 18, wherein said orienting means are configured as an annular plate and delimit a through opening of dimensions roughly corresponding to those of said through openings of said sides of said humeral section.

21. The spacer device according to claim 20, wherein said annular plate has a minimum thickness at its own proximal section intended, in use, to be housed in said engagement seat facing said in use front wall of said humeral section.

22. The spacer device according to claim 21, wherein said annular plate has, at said proximal section, a perimeter configuration with straight sections substantially corresponding to the internal configuration of said seat between said front in use wall and rear in use wall.

23. The spacer device according to claim 21, wherein said annular plate has a flange in a distal section opposite to said proximal section.

24. The spacer device according to claim 20, wherein said orienting means are obtained integral with said at least one ulnar section.

25. The spacer device according to claim 20, wherein said through opening is aligned with a through opening of said at least one ulnar section.

26. The spacer device according to claim 18, wherein said orienting means have a substantially circular crown shaped cross section.

27. The spacer device according to claim 5, wherein in a first working position, said proximal end of said at least one ulnar section is in said engagement seat juxtaposed with said side and, therefore, has its longitudinal axis (x-x) shifted by $-\theta°$ from said axis (y-y) of said humeral section.

28. The spacer device according to claim 5, wherein in a second working position, said proximal end of said at least one ulnar section is in said engagement seat juxtaposed with said side and, therefore, has its longitudinal axis (x-x) shifted by $+\theta°$ from said axis (y-y) of said humeral section.

29. A method of assembling a spacer device according to claim 1, comprising the following operating steps:

arranging at least one humeral section, at least one ulnar section, at least articulation means between said at least one humeral section and said at least one ulnar section;

inserting said proximal end of said at least one ulnar section in said engagement seat of said at least one humeral section, with the through opening of the respective sections aligned with each other;

if said spacer device is intended to be implanted in the upper right limb of a patient, arranging said at least one ulnar section so that it has its longitudinal axis (x-x) shifted by an angle of $-\theta°$ with respect to the axis (y-y) of said at least one humeral section;

alternatively, if said spacer device is intended to be implanted in the upper right limb of a patient, arranging said at least one ulnar section so that it has its longitudinal axis (x-x) shifted by an angle of $+\theta°$ with respect to the axis (y-y);

inserting orientation means in said engagement seat between said ulnar section and one of the two sides of the humeral section with the respective through opening aligned with through openings of the two sides and the ulnar section; and inserting said articulation means in said through openings of said at least one ulnar section and at least one humeral section.

30. The method of assembly of a spacer device according to claim 24, comprising the following steps:

arranging at least one humeral section, at least one ulnar section, at least articulation means between said at least one humeral section and said at least one ulnar section, said at least one ulnar section being integral with said orienting means;

inserting said proximal end of said at least one ulnar section in said engagement seat of said at least one humeral section, with the through openings of the respective sections aligned with each other; and inserting said articulation means in said through openings of said at least one ulnar section and at least one humeral section.

31. A spacer device for the treatment of infections at the elbow joint, comprising:

at least one ulnar section, comprising a stem portion extending along a substantially longitudinal axis (x-x) between a proximal end and a distal end;

at least one humeral section, comprising a stem portion extending along a substantially longitudinal axis (y-y) between a proximal end and a distal end;

at least one engagement seat between said distal end of said at least one humeral section and said proximal end of said at least one ulnar section, said at least one engagement seat being delimited by said at least one humeral section; and articulation means between said distal end of said at least one humeral section and said proximal end of said at least one ulnar section, positionable along an axis (z-z) orthogonal to said substantially longitudinal axis (y-y) of said at least one humeral section;

wherein said proximal end of said at least one ulnar section is engageable in said engagement seat said proximal end having its own longitudinal axis (x-x) nonorthogonal to said axis (z-z) of said articulation means, according to at least two opposed working positions, according to whether said spacer device is designed to be implanted in the right or in the left upper limb of a patient, wherein said at least one ulnar section comprises an annular plate being positionable in said at least one engagement seat and having a proximal section facing a front wall of the humeral section and a distal section opposite to said proximal section, wherein said annular plate comprises a flange in the distal section, wherein the annular plate has a thickness at the distal section which is greater than a thickness at the proximal section.

* * * * *